(12) United States Patent
Simon et al.

(10) Patent No.: US 12,042,647 B2
(45) Date of Patent: *Jul. 23, 2024

(54) CATHETER DEVICE HAVING A COUPLING DEVICE FOR A DRIVE DEVICE

(71) Applicant: Ecp Entwicklungsgesellschaft Mbh, Aachen (DE)

(72) Inventors: Cornelia Simon, Aachen (DE); Julia Honselmann, Aachen (DE); Jens Baumgaertel, Aachen (DE); Reiner Liebing, Aachen (DE)

(73) Assignee: ECP Entwicklungsgesellschaft mbH, Aachen (DE)

( * ) Notice: Subject to any disclaimer, the term of this patent is extended or adjusted under 35 U.S.C. 154(b) by 216 days.

This patent is subject to a terminal disclaimer.

(21) Appl. No.: 17/404,102

(22) Filed: Aug. 17, 2021

(65) Prior Publication Data

US 2022/0032034 A1  Feb. 3, 2022

Related U.S. Application Data

(63) Continuation of application No. 16/204,123, filed on Nov. 29, 2018, now Pat. No. 11,116,960, which is a (Continued)

(30) Foreign Application Priority Data

Aug. 6, 2009 (EP) ..................................... 09075349

(51) Int. Cl.
*A61M 60/416* (2021.01)
*A61M 60/13* (2021.01)
(Continued)

(52) U.S. Cl.
CPC .......... *A61M 60/414* (2021.01); *A61M 60/13* (2021.01); *A61M 60/216* (2021.01);
(Continued)

(58) Field of Classification Search
None
See application file for complete search history.

(56) References Cited

U.S. PATENT DOCUMENTS 3,510,229 A  5/1970  Smith
3,568,659 A  3/1971  Karnegis
(Continued)

FOREIGN PATENT DOCUMENTS

CA   1008330 A    4/1977
CA   2311977 A1   12/2000
(Continued)

OTHER PUBLICATIONS

International Search Report and Written Opinion for International Application No. PCT/EP2010/004102 dated Aug. 18, 2020 (4 pages).

*Primary Examiner* — Erica S Lee
(74) *Attorney, Agent, or Firm* — Botos Churchill IP Law LLP

(57) ABSTRACT

Catheter device, having a hollow catheter in the catheter cavity of which a moveable shaft is guided, having a proximal coupling device, for detachable coupling of a drive device, the coupling device having a coupling cavity which is open towards the drive device and into which the shaft or an extension of the shaft protrudes with a connection element for mechanical coupling of a motor shaft, the coupling cavity having a germ barrier for reducing the pathogenicity of pathogenic substances or microorganisms.

20 Claims, 3 Drawing Sheets

Related U.S. Application Data continuation of application No. 13/261,151, filed as application No. PCT/EP2010/004102 on Jun. 30, 2010, now Pat. No. 10,172,985.

(60) Provisional application No. 61/231,787, filed on Aug. 6, 2009.

(51) Int. Cl.
*A61M 60/216* (2021.01)
*A61M 60/414* (2021.01)
*A61M 60/829* (2021.01)
*A61B 17/00* (2006.01)
*A61B 17/3207* (2006.01)
*A61M 25/01* (2006.01)
*A61M 60/148* (2021.01)
*A61M 60/419* (2021.01)

(52) U.S. Cl.
CPC . *A61M 60/829* (2021.01); *A61B 2017/00889* (2013.01); *A61B 17/320758* (2013.01); *A61M 25/0105* (2013.01); *A61M 60/148* (2021.01); *A61M 60/419* (2021.01)

(56) References Cited

U.S. PATENT DOCUMENTS

| | | | |
|---|---|---|---|
| 3,802,551 A | 4/1974 | Somers | |
| 3,812,812 A | 5/1974 | Hurwitz | |
| 4,014,317 A | 3/1977 | Bruno | |
| 4,207,028 A | 6/1980 | Ridder | |
| 4,559,951 A | 12/1985 | Dahl et al. | |
| 4,563,181 A | 1/1986 | Wijayarathna et al. | |
| 4,623,329 A | 11/1986 | Drobish et al. | |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A * | 6/1988 | Kensey | A61M 60/13 600/16 |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A | 11/1990 | Hwang et al. | |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A | 3/1992 | Schwartz et al. | |
| 5,097,849 A | 3/1992 | Kensey et al. | |
| 5,108,411 A | 4/1992 | Mckenzie | |
| 5,112,292 A | 5/1992 | Hwang et al. | |
| 5,113,872 A | 5/1992 | Jahrmarkt et al. | |
| 5,117,838 A | 6/1992 | Palmer et al. | |
| 5,118,264 A | 6/1992 | Smith | |
| 5,145,333 A | 9/1992 | Smith | |
| 5,163,910 A | 11/1992 | Schwartz et al. | |
| 5,169,378 A | 12/1992 | Figuera | |
| 5,183,384 A | 2/1993 | Trumbly | |
| 5,191,888 A | 3/1993 | Palmer et al. | |
| 5,201,679 A | 4/1993 | Velte et al. | |
| 5,263,930 A * | 11/1993 | Ensminger | A61M 39/0606 604/288.03 |
| 5,275,580 A | 1/1994 | Yamazaki | |
| 5,358,485 A * | 10/1994 | Vance | A61B 17/320758 606/159 |
| 5,368,035 A | 11/1994 | Hamm et al. | |
| 5,373,619 A | 12/1994 | Fleischhacker et al. | |
| 5,376,114 A | 12/1994 | Jarvik | |
| 5,501,574 A | 3/1996 | Raible | |
| 5,531,789 A | 7/1996 | Yamazaki et al. | |
| 5,637,267 A | 6/1997 | Lo et al. | |
| 5,701,911 A | 12/1997 | Sasamine et al. | |
| 5,755,784 A | 5/1998 | Jarvik | |
| 5,776,190 A | 7/1998 | Jarvik | |
| 5,813,405 A | 9/1998 | Montano et al. | |
| 5,820,571 A | 10/1998 | Erades et al. | |
| 5,851,174 A | 12/1998 | Jarvik et al. | |
| 5,855,203 A | 1/1999 | Matter | |
| 5,882,329 A | 3/1999 | Patterson et al. | |
| 5,888,241 A | 3/1999 | Jarvik | |
| 5,938,672 A | 8/1999 | Nash | |
| 6,030,397 A | 2/2000 | Monetti et al. | |
| 6,129,704 A | 10/2000 | Forman et al. | |
| 6,129,734 A * | 10/2000 | Shturman | F16D 43/14 606/159 |
| 6,152,693 A | 11/2000 | Olsen et al. | |
| 6,165,163 A * | 12/2000 | Chien | A61M 25/0053 604/524 |
| 6,168,433 B1 | 1/2001 | Hamlin | |
| 6,168,624 B1 | 1/2001 | Sudai | |
| 6,221,061 B1 | 4/2001 | Engelson et al. | |
| 6,254,359 B1 | 7/2001 | Aber | |
| 6,302,910 B1 | 10/2001 | Yamazaki et al. | |
| 6,308,632 B1 | 10/2001 | Shaffer | |
| 6,336,939 B1 | 1/2002 | Yamazaki et al. | |
| 6,346,120 B1 | 2/2002 | Yamazaki et al. | |
| 6,387,125 B1 | 5/2002 | Yamazaki et al. | |
| 6,503,224 B1 | 1/2003 | Forman et al. | |
| 6,506,025 B1 | 1/2003 | Gharib | |
| 6,508,787 B2 | 1/2003 | Erbel et al. | |
| 6,517,315 B2 | 2/2003 | Belady | |
| 6,527,521 B2 | 3/2003 | Noda | |
| 6,533,716 B1 | 3/2003 | Schmitz-rode et al. | |
| 6,537,030 B1 | 3/2003 | Garrison | |
| 6,537,315 B2 | 3/2003 | Yamazaki et al. | |
| 6,589,164 B1 | 7/2003 | Flaherty | |
| 6,592,612 B1 | 7/2003 | Samson et al. | |
| 6,652,548 B2 | 11/2003 | Evans et al. | |
| 6,719,791 B1 | 4/2004 | Nuesser et al. | |
| 6,860,713 B2 | 3/2005 | Hoover | |
| 6,945,977 B2 | 9/2005 | Demarais et al. | |
| 6,981,942 B2 | 1/2006 | Khaw et al. | |
| 7,022,100 B1 | 4/2006 | Aboul-hosn et al. | |
| 7,027,875 B2 | 4/2006 | Siess et al. | |
| 7,074,018 B2 | 7/2006 | Chang | |
| 7,179,273 B1 | 2/2007 | Palmer et al. | |
| 7,393,181 B2 | 7/2008 | Mcbride et al. | |
| 7,467,929 B2 | 12/2008 | Nuesser et al. | |
| 7,731,675 B2 | 6/2010 | Aboul-hosn et al. | |
| 7,927,068 B2 | 4/2011 | Mcbride et al. | |
| 7,934,909 B2 | 5/2011 | Nuesser et al. | |
| 8,035,487 B2 | 10/2011 | Malackowski | |
| 2002/0123661 A1 | 9/2002 | Verkerke et al. | |
| 2003/0093103 A1 | 5/2003 | Malackowski et al. | |
| 2003/0135086 A1 | 7/2003 | Khaw et al. | |
| 2003/0231959 A1 | 12/2003 | Snider | |
| 2004/0044266 A1 | 3/2004 | Siess et al. | |
| 2004/0046466 A1 | 3/2004 | Siess et al. | |
| 2004/0093074 A1 | 5/2004 | Hildebrand et al. | |
| 2004/0215222 A1 | 10/2004 | Krivoruchko | |
| 2004/0215228 A1 | 10/2004 | Simpson et al. | |
| 2004/0238776 A1 * | 12/2004 | Peters | A61M 39/1011 604/905 |
| 2006/0008349 A1 | 1/2006 | Khaw | |
| 2006/0062672 A1 | 3/2006 | Mcbride et al. | |
| 2006/0195004 A1 | 8/2006 | Jarvik | |
| 2008/0086042 A1 | 4/2008 | Brister et al. | |
| 2008/0132747 A1 | 6/2008 | Shifflette | |
| 2008/0262584 A1 | 10/2008 | Bottomley et al. | |
| 2008/0306327 A1 | 12/2008 | Shifflette | |
| 2009/0018566 A1 | 1/2009 | Escudero et al. | |
| 2009/0060743 A1 | 3/2009 | Mcbride et al. | |
| 2009/0093764 A1 | 4/2009 | Pfeffer et al. | |
| 2009/0093796 A1 | 4/2009 | Pfeffer et al. | |
| 2009/0112128 A1 * | 4/2009 | Schiff | A61B 5/14539 600/585 |
| 2009/0257910 A1 | 10/2009 | Segal | |
| 2009/0270812 A1 | 10/2009 | Litscher et al. | |
| 2009/0292304 A1 | 11/2009 | Malackowski et al. | |

(56) References Cited

U.S. PATENT DOCUMENTS

| | | |
|---|---|---|
| 2010/0041939 A1 | 2/2010 | Siess |
| 2010/0211020 A1 | 8/2010 | Layton |
| 2010/0268017 A1 | 10/2010 | Siess |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 A1 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 480102 A1 | 4/1992 |
| EP | 560000 A2 | 9/1993 |
| EP | 629412 A2 | 12/1994 |
| EP | 768091 A1 | 4/1997 |
| EP | 884064 A2 | 12/1998 |
| EP | 914171 A2 | 5/1999 |
| EP | 0916359 A1 | 5/1999 |
| EP | 951302 A2 | 10/1999 |
| EP | 1019117 A1 | 7/2000 |
| EP | 1066851 A1 | 1/2001 |
| EP | 1114648 A2 | 7/2001 |
| EP | 1337288 A1 | 8/2003 |
| EP | 1651290 A1 | 5/2006 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 A1 | 10/2000 |
| WO | 0107760 A1 | 2/2001 |
| WO | 2001007787 A1 | 2/2001 |
| WO | 0160427 A2 | 8/2001 |
| WO | 2001083016 A2 | 11/2001 |
| WO | 2003057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

\* cited by examiner

CATHETER DEVICE HAVING A COUPLING DEVICE FOR A DRIVE DEVICE

CROSS-REFERENCE TO RELATED APPLICATIONS

This application is a continuation of U.S. application Ser. No. 16/204,123, filed Nov. 29, 2018, now U.S. Pat. No. 11,116,960, which is a continuation of U.S. application Ser. No. 13/261,151, filed Mar. 30, 2012, now U.S. Pat. No. 10,172,985 B2, which is a national phase entry under 35 U.S.C. § 371 of International Application No. PCT/EP2010/004102, filed Jun. 30, 2010, and published as International Publication No. WO 2011/015262 A1, which claims priority to U.S. Provisional Application No. 61/231,787, filed Aug. 6, 2009, and European Patent Application No. 09075349.2, filed Aug. 6, 2009, the entire disclosures of which are hereby incorporated herein by reference.

BACKGROUND OF THE INVENTION

The invention resides in the field of mechanics or mechanical engineering and precision engineering and can be used in particular in the construction of small instruments for invasive use in medical technology.

BRIEF SUMMARY OF THE INVENTION

Instruments which can be actuated from outwith the body via flexible shafts are often used in particular in minimally invasive medicine. These shafts are normally guided through catheters which are introduced into the body through small openings or naturally occurring body vessels under particularly sensitive surrounding conditions.

A particular application form resides for example in the actuation of liquid pumps in microconstructional form which are used for example as heart pumps and which can be introduced into a ventricle with a heart catheter.

Particular requirements thereby reside not only in the small constructional size of the corresponding pumps, as also when using other microinvasive instruments actuated via such a shaft, but also during operation of the flexible shaft. In particular at the high speeds of rotation often required, intensive deformation of the shaft takes place which causes high mechanical and thermal stress. Therefore, it is normal to fill corresponding hollow catheters with a biocompatible liquid for lubrication and cooling of the shaft.

In order to ensure shielding of such a hollow catheter relative to the body exterior, frequently motor drives with magnetic couplings are used as drives at the proximal end of the shaft, externally of the body, which drives act through hermetically sealed housing walls of corresponding shaft connection housings.

Magnetic couplings of this type are however substantially more expensive and sensitive relative to conventional couplings. In order to transmit the required torque reliably, a significant over-dimensioning is required because of the normally low efficiency of such a magnetic coupling.

In addition, normally the motor drive together with the hollow catheter and the shaft and possibly a connected instrument must be certificated. This is particularly inefficient if at least one of the parts, either the motor drive or the catheter, is intended to be used multiple times and if these are only assembled during actual use.

In connection with a hollow catheter which houses a guide wire and a rotating imaging ultrasonic device, sterile shielding of an end region of a slowly rotating shaft is known from the U.S. Pat. No. 5,368,035, which shaft essentially comprises a sleeve and is assembled with the hollow catheter if required or is again detached from the latter in order to push an element via the guide wire. The sleeve prevents toxic substances from passing through in that it forms a mechanical obstacle for these substances.

The object underlying the present invention is to produce a catheter device having a hollow catheter and a moveable shaft which, in a constructionally simple and economical manner, can be coupled reliably to a corresponding drive unit whilst maintaining the normal requirements for asepsis.

The object is achieved according to the invention by the features of patent claim 1.

Basically, the object within the scope of the invention is achieved by provision of means for reducing the pathogenicity of pathogenic substances or microorganisms in the proximal region of a hollow catheter of a catheter device, in particular a blood pump device.

According to patent claim 1, a hollow catheter which can be introduced into a body, in particular for a blood pump, is thereby provided with a catheter cavity in which a moveable shaft is guided, and also a proximal coupling device for preferably detachable coupling of a drive device. The coupling device has a coupling cavity which is open towards the drive device and into which the shaft or an extension of the shaft protrudes. The shaft is preferably provided with a connection element for mechanical coupling of a motor shaft. The coupling device, in particular the coupling cavity, thereby has means for reducing the pathogenicity of pathogenic substances or microorganisms, preferably in the form of a germ barrier.

More detail is given further on with respect to possible types and modes of operation of germ barriers. There are thereby understood as germ barriers not only those means which basically destroy all germs but also those means which reduce and partially destroy and/or suppress living germs.

It is thereby important that the coupling cavity per se is open towards the motor side so that the motor shaft can be coupled in an easy and simple manner to the shaft to be actuated or a corresponding extension or connection part. The corresponding connection part can thereby provide in addition a length compensation possibility for example by form-fit adaptation to the motor shaft in the direction of rotation and axial displaceablity of the connection part relative to the motor shaft. The coupling cavity can be closed, during connection of a drive direction, advantageously by corresponding elements of the drive device, for example a sleeve which is inserted in a form-fit and in a seal around a coupling sleeve forming the coupling cavity or into said sleeve. If the coupling sleeve is configured as a cylindrical sleeve, a corresponding cover advantageously provided with a seal can be configured on the sides of the drive device.

The coupling cavity can be sealed by a shaft seal relative to the catheter cavity. As a result, shielding relative to the catheter cavity, in addition to a germ barrier, is produced, which in fact per se normally does not fulfil the requirements for clinical asepsis but minimizes substance exchange between the coupling cavity and the catheter cavity and hence reduces the requirements on the germ barrier or makes its effect more reliable. The design of the shaft seal is thereby all the more difficult the more rapidly the shaft is intended to rotate. In the present case, the shaft can be provided for operation at least 10,000 rpm.

A particular embodiment of the means for reducing the pathogenicity of pathogenic substances or microorganisms, in particular in the form of a germ barrier, provides that these are configured as a partial chamber of the coupling cavity which can be filled with a germicidal gel. This partial chamber is penetrated by the shaft so that no living germs or those only in a reduced number can migrate in particular along the shaft. The use of a gel ensures, on the one hand, that the latter does not flow because of its thixotropic properties, i.e., remains stationary, and, on the other hand, cavities which could possibly be produced are constantly closed. Instead of the gel, also a viscous liquid can possibly be used.

It can thereby be provided that the partial chamber is delimited, on the drive side, by a seal or a bearing for the shaft. In addition to the corresponding support and guidance of the shaft, the gel or possibly liquefied partial quantities of the gel is hence retained in the partial chamber.

Furthermore, a shaft or a bearing can also be provided on the catheter cavity side which represents further guidance for the shaft so that the partial chamber is delimited axially on both sides with respect to the shaft respectively by a bearing or a shaft.

Advantageously, the partial chamber has a filling opening through which gel can be introduced when the drive device is coupled. This means that, for example in the coupling sleeve, a closeable opening, e.g., with a connection pipe, is provided, through which the gel can be introduced before or after coupling of the drive and hence the germ barrier can be provided.

A further advantageous embodiment of the means for reducing the pathogenicity of pathogenic substances or microorganisms, in particular in the form of a germ barrier, provides that the latter is configured as an irradiation chamber which is penetrated by the shaft or an extension of the shaft and can be supplied with germicidal radiation, in particular light, preferably UV light, further preferred light of a wavelength between 255 and 265 nm or X-rays. The corresponding irradiation chamber can be configured as a partial chamber of the coupling cavity or include this in its entirety. It can be provided that reflection elements for the radiation are provided in order to be able to reach all regions of the irradiation chamber with as few radiation sources as possible. The constitution of such reflection elements depends inter alia also upon the wavelength of the radiation which is used.

In particular, the irradiation chamber can advantageously have a radiation window which is permeable for the germicidal radiation and hermetically seals the irradiation chamber.

A radiation source, in particular an ultraviolet diode, can be inserted in front of the radiation window. If a corresponding radiation window is integrated in the diode, a sealing receiving means for the diode can also serve in a simple manner as radiation window. A corresponding radiation source can be disposed, if necessary, also in the irradiation chamber itself.

In order to supply the entire irradiation chamber reliably with radiation, also two or more radiation windows can be provided with corresponding diodes.

The coupling sleeve which surrounds the coupling cavity at least partially is advantageously sealed hermetically with the hollow catheter, in particular is connected non-detachably, preferably in one piece. The connection can be produced by the known integral connection methods, such as gluing and welding.

If the catheter device is provided with a drive, then a cover sleeve which is connected in one piece to a drive housing or at least in a sealing manner can be provided and can be pushed onto the coupling sleeve from outside. Hence, in particular if the inner diameter of the cover sleeve corresponds to the outer diameter of the coupling sleeve, a long sealing region between the coupling sleeve and the cover sleeve is provided.

The corresponding seal can be improved further by inserting an elastomer seal between the coupling sleeve and the cover sleeve.

The cover sleeve advantageously has a shaft for the radiation source, which shaft opens in front of the radiation window after assembly and into which the radiation source can be inserted.

For a reliable and easily producible connection between the hollow catheter and the coupling device, on the one hand, and the drive device, on the other hand, a locking connection device can advantageously be provided so that the corresponding connection can also be easily detached. This is particularly advantageous if one of the elements, normally the drive device, is intended to be used multiple times and the parts are separated after use on one patient. The catheter-side elements are normally delivered in sterile packaging, used on the patient after unpacking and connected to an individually sterilized drive device.

In order to increase the safety of the patient and the functional capacity of the shaft further, it can be provided advantageously in addition that, in addition to the mentioned germ barrier, an additional germ barrier is provided on the distal side of the shaft seal and of the coupling cavity, said germ barrier being able to be configured for example in the shape of a shaft rinsing device. In order to assist their flexibility, the normally used shafts are generally combined and twisted from thinner strands so that a spindle-like surface structure is produced, which leads, at rapid rotation, to conveyance of the fluid situated in the catheter along the shaft. This effect is in general not necessarily desired but is scarcely avoidable. Correspondingly, new fluid must subsequently flow from the drive-side end of the catheter. This can be delivered by a corresponding shaft rinsing device which however requires special elements in order to convey the fluid into the catheter chamber without germs and bubbles. In order to form optimized flow conditions within a shaft rinsing device, a so-called counterflow sleeve for example can be provided there, which sleeve rotates with the shaft and has drive elements for the fluid, for example in the form of blades which act counter to the conveying direction acting on the fluid by means of the shaft surface structure.

In the cooperation of the germ barrier with this additional germ barrier, additional safety for the patient is produced.

BRIEF DESCRIPTION OF THE DRAWINGS

In the following, the invention is shown and subsequently described in a drawing with reference to an embodiment. There are thereby shown FIG. 1 in a schematic longitudinal section, the end region of a hollow catheter on the drive- or proximal side with a connected drive and a germ barrier in the form of a gel-filled partial chamber, FIG. 2 likewise schematically in longitudinal section, a similar device to FIG. 1, the germ barrier being configured as an irradiation chamber, and also FIG. 3 schematically, the configuration of an additional germ barrier in the form of a shaft rinsing device in the end region of the hollow catheter.

DETAILED DESCRIPTION

Figure 1:
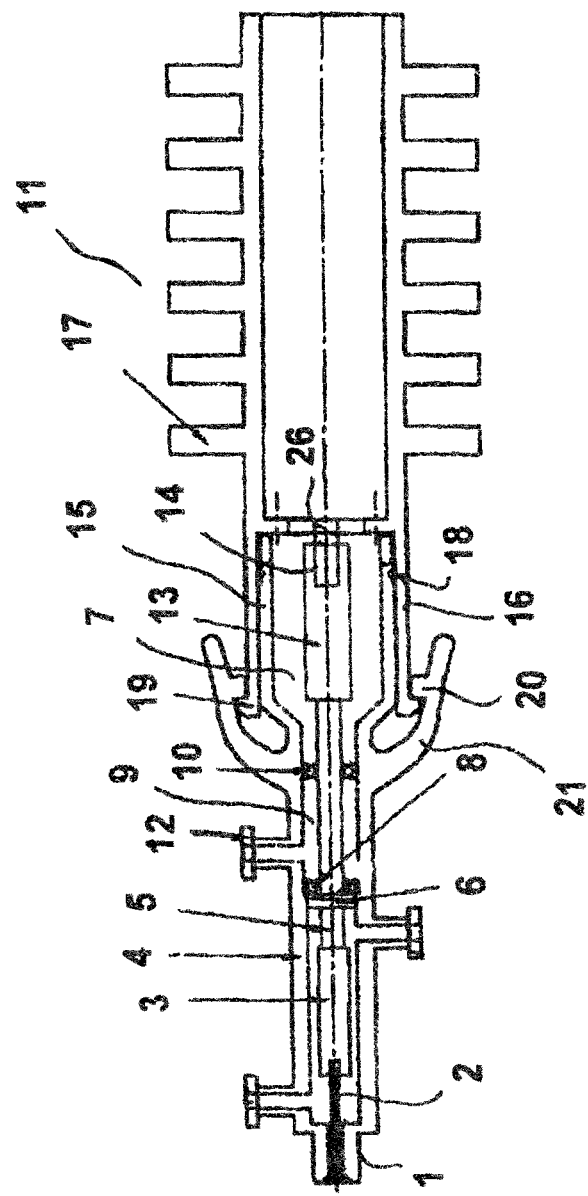

On the left side, FIG. 1 shows the hollow catheter 1 with the flexible shaft 2 which is guided in the catheter cavity and is connected in a non-rotatable manner to a first connection part 3. The first connection part 3 is situated in the region of a shaft rinsing device 4 which is dealt with in more detail further on in connection with FIG. 3. On the other side of the first connection part 3, an extension 5 of the shaft 2 is connected and is guided through a shaft seal 6 in a sealed manner from the shaft rinsing device 4 to a coupling cavity 7.

On the other side of the shaft seal 6, a first bearing 8 is connected, which guides the shaft extension 5 and delimits a partial chamber 9 which can be filled or is filled with gel on the catheter side. A second bearing 10 delimits the partial chamber 9 towards the drive device 11.

A filling opening 12 through which the partial chamber 9 can be filled with a germicidal gel or a viscous germicidal liquid is provided. The shaft extension 5 extends up to a second connection part 13 and is connected securely thereto.

The second connection part 13 has a polygonal opening on the inside, for example a hexagonal opening, into which a corresponding hexagon 14 of a motor shaft can be introduced in a non-rotatable manner but axially displaceable for length compensation. The coupling chamber 7 is surrounded in total by a coupling sleeve 15 which can be introduced into a corresponding cover sleeve 16 of the drive housing 17 and can be sealed thereon by means of an elastomer seal 18. The cover sleeve 16 has locking noses 19 which engage behind corresponding shoulder parts 20 of locking arms 21 of the coupling sleeve 15 and produce a detachable connection between the drive 11 and the catheter.

The represented device has the effect that the coupling cavity 7 which is open on the drive side during mounting of the drive device 11 is hermetically separated from the shaft rinsing device and the catheter cavity by a gel barrier in the partial chamber 9, the shaft extension 5 being embedded in the gel so that no germs can migrate from the open end of the coupling cavity towards the catheter cavity along the shaft extension 5. Hence asepsis can be ensured even when coupling the drive device 11 in a chamber which is not completely aseptic.

Figure 2:
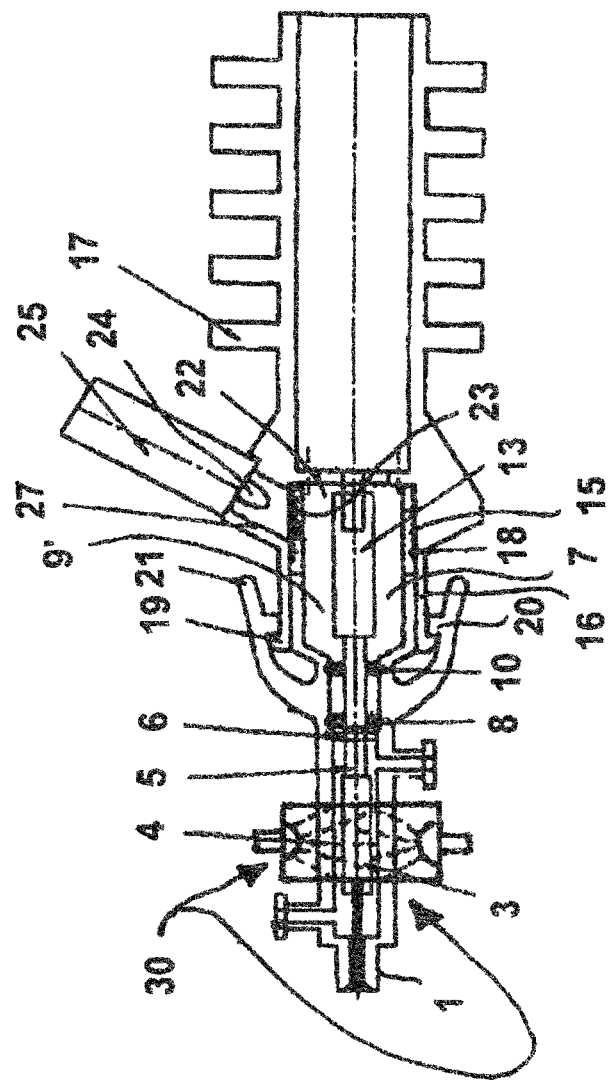

In FIG. 2 elements which remain the same or perform the same functions relative to FIG. 1 are provided with the same reference numbers. In FIG. 2, in contrast to FIG. 1, an irradiation chamber 9' is provided as partial chamber of the coupling cavity 7 and extends from the shaft seal 6 up to the drive-side opening 22 of the coupling cavity. Said irradiation chamber is characterized inter alia by a radiation window 23 which consists of for example Plexiglas or another material which is permeable for the corresponding radiation, in particular ultraviolet radiation. The radiation window 23 is fitted into the coupling sleeve 15 in a hermetically sealed manner.

On the drive side, a shaft 27 is integrated in the cover sleeve 16, into which shaft a radiation source in the form of a UV diode 24 can be inserted, which diode is fitted in an actuation unit 25 and is connected thereto.

In addition, reflection elements for the UV radiation, which are not represented in detail, can be provided in the partial chamber 9'.

The two represented embodiments of a germ barrier can also be combined with each other such that, in addition to the irradiation chamber 9', a germicidal gel is inserted between the bearings 8, 10, as described according to FIG. 1.

Basically, also alternatively or additionally to the above-described types of germ barriers, a radiation source for germicidal radiation, advantageously a UV radiation source, can be provided at any position along the shaft or the hollow catheter, even on the distal side of the last bearing seal. The irradiation device can be constructed like the represented germ barrier on the coupling cavity; however, it can also be configured as a cover sleeve with a radiation source directed inwardly towards the catheter. It can be provided for example at the level of the shaft rinsing device, as represented in FIG. 2, and provided with the reference number 30. The radiation sources themselves are designated there with 31, 32. The sleeve can be at least partially silvered on the inside in order to reflect and diffuse the radiation. The energy supply of the radiation source(s) can be produced by electrical lines extending parallel to the catheter. This configuration of a germ barrier demands a partially radiation-permeable design of the hollow catheter. It can be applied basically both to catheters which have a drive shaft and without drive shaft, for example also in the case of hoses conducting a fluid and introduced into a body.

The motor which is accommodated in the drive housing 17 and has a motor shaft 26 which ends in the hexagon 14 and is actuated electrically, is not represented in detail in the drawing.

Furthermore, an instrument which is connected to the shaft 2 and can be actuated by means of the latter, such as for example a micropump which can be used as heart pump, or a microcutter, is not represented at the distal end.

Figure 3:
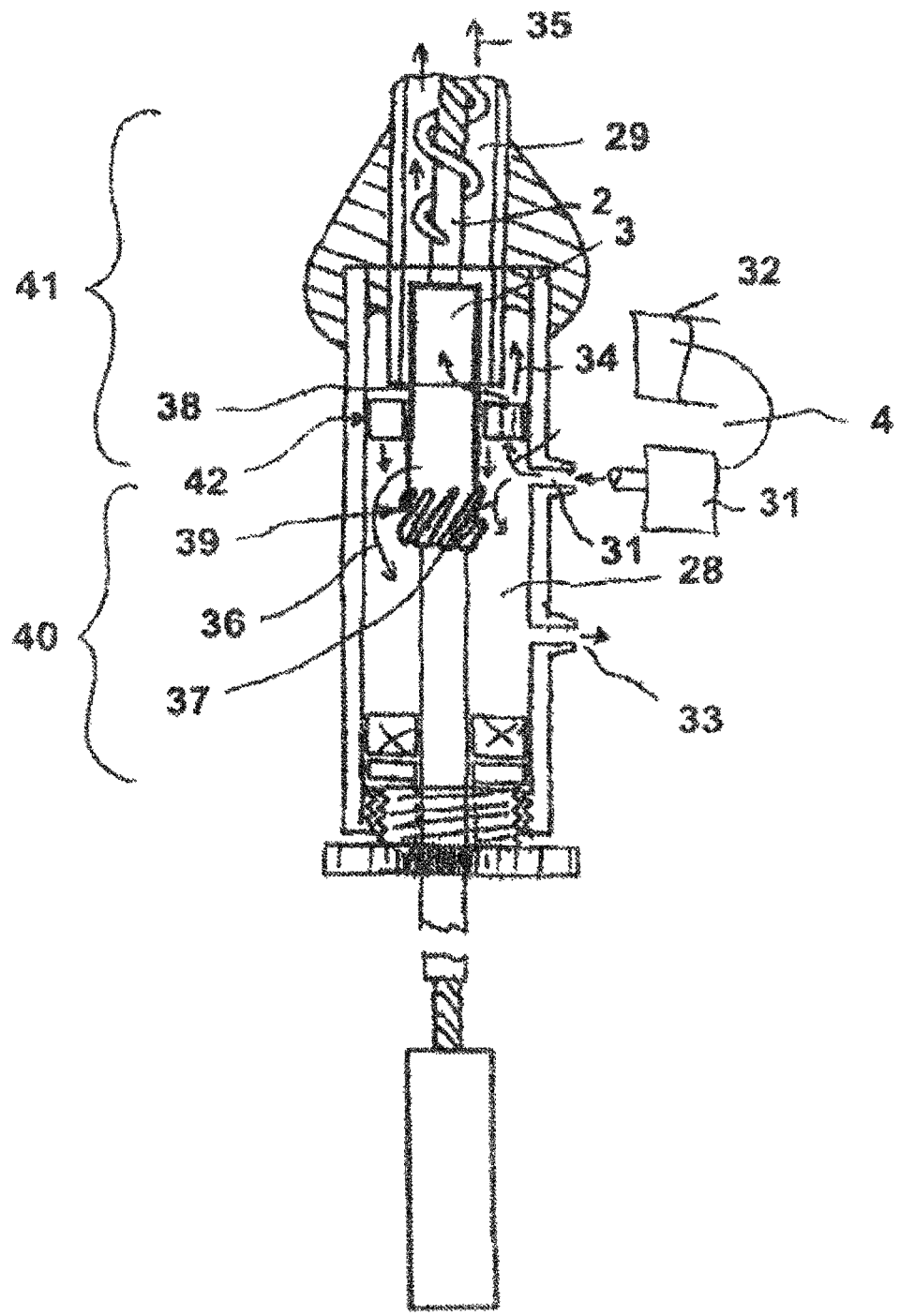

The shaft rinsing device which is connected on the catheter side to the germ barrier is represented in more detail in FIG. 3. The germ barrier itself has been omitted in FIG. 3 for the sake of clarity.

The shaft rinsing device 4 has the first connection part 3 to which the shaft 2 is connected non-rotatably. A rinsing chamber 28 which is connected to the catheter cavity 29 is provided. An aseptic or germicidal rinsing liquid can be introduced into the rinsing chamber 28 via a filling opening 30 by means of a pump 31 which is connected to a reservoir 32. The liquid is discharged again partially through an outlet opening 33 which also serves for ventilation.

The rinsing liquid is distributed, according to the illustrated flow direction arrows 34, 35, in the direction of the catheter cavity and along the shaft 2 and also from the filling opening 30 in the opposite direction, as represented by the arrows 36, 37, towards the drive side. This is effected in particular by the counterflow sleeve 38 which has drive elements 39 is the form of blade-like webs and which rotates with the first connection part 3. The counterflow sleeve 38 can be connected also in one piece to the connection part 3.

Within the rinsing chamber 28, a slight excess pressure which prevents or at least reduces penetration of air through the ventilation opening 33 is produced by the counterflow sleeve in the axial region which is designated with 40. At the same time, the pressure is lowered slightly in the axial chamber designated with 41 and in the entire catheter chamber 39 and hence the flow of rinsing medium in the direction of the shaft towards the distal end is prevented. This is desirable for reducing the substance throughput along the shaft.

A bearing 42 which is permeable for the rinsing liquid is provided for mounting the counterflow sleeve 38.

In particular together with the germ barriers represented in FIGS. 1 and 2 in more detail, the rinsing device in addition improves the asepsis of the catheter and ensures a low-abrasion and reliable operation of the shaft even at high speeds of rotation.

The invention claimed is:
1. A catheter device comprising:
 a catheter having a lumen, a proximal end, and a distal end;

a first housing having a proximal end and a distal end, the distal end of the housing being coupled to the proximal end of the catheter, and the first housing comprising:
- a catheter cavity in communication with the lumen of the catheter;
- a coupling cavity; and
- a germicidal gel within the coupling cavity; and
- a first seal between the catheter cavity and the coupling cavity, the first seal being configured to prevent the germicidal gel migrating from the coupling cavity to the catheter cavity;

a second housing configured to be releasably coupled to the first housing;

a motor arranged within the second housing, the motor having a motor shaft extending through a wall of the second housing; and a drive shaft having a proximal end and a distal end, the proximal end of the drive shaft being configured to be releasably coupled to the motor shaft in the coupling cavity when the second housing is releasably coupled to the first housing, and the drive shaft extending at least from the coupling cavity, through the first seal, to the catheter cavity.

2. The catheter device of claim 1, wherein the drive shaft extends at least partially into the lumen of the catheter.

3. The catheter device of claim 2, wherein the drive shaft comprises a plurality of twisted strands.

4. The catheter device of claim 1, wherein the distal end of the drive shaft is coupled within the catheter cavity to a proximal end of a second drive shaft, and wherein the second drive shaft extends at least partially into the lumen of the catheter.

5. The catheter device of claim 4, wherein the second drive shaft comprises a plurality of twisted strands.

6. The catheter device of claim 1, wherein the drive shaft is configured to be axially displaceable relative to the motor shaft while the drive shaft is releasably coupled to the motor shaft.

7. The catheter device of claim 1, wherein the first housing or the second housing further comprises a second seal configured to prevent fluid from entering or escaping the coupling cavity when the second housing is releasable coupled to the first housing.

8. The catheter device of claim 1, wherein the first housing further comprises a first opening.

9. The catheter device of claim 8, further comprising a pump configured to pump a rinsing liquid into the catheter cavity through the first opening.

10. The catheter device of claim 9, wherein the first housing further comprises a second opening, the second opening being configured to allow the rinsing liquid to exit the catheter cavity.

11. The catheter device of claim 10, further comprising a counterflow sleeve coupled to the drive shaft, the counterflow sleeve having at least one blade configured to induce a first flow of the rinsing liquid out of the second opening of the first housing when the motor drives the drive shaft.

12. The catheter device of claim 11, wherein the drive shaft extends at least partially into the lumen of the catheter, and wherein the drive shaft is further configured to induce a second flow of the rinsing liquid into the lumen of the catheter when the motor drives the drive shaft.

13. The catheter device of claim 11, wherein the first seal is further configured to prevent the rinsing liquid migrating from the catheter cavity into the coupling cavity.

14. The catheter device of claim 9, further comprising a counterflow sleeve coupled to the drive shaft, the counterflow sleeve having at least one blade configured to induce a first flow of the rinsing liquid away from the proximal end of the catheter when the motor drives the drive shaft.

15. The catheter device of claim 14, wherein the drive shaft extends at least partially into the lumen of the catheter, and wherein the drive shaft is further configured to induce a second flow of the rinsing liquid into the lumen of the catheter when the motor drives the drive shaft.

16. The catheter device of claim 14, wherein the first seal is further configured to prevent the rinsing liquid migrating from the catheter cavity into the coupling cavity.

17. The catheter device of claim 1, wherein the first housing further comprises a radiation window, the radiation window being permeable to ultraviolet radiation and impermeable to liquid.

18. The catheter device of claim 17, further comprising a radiation source positioned outside the coupling cavity and adjacent to the radiation window.

19. The catheter device of claim 18, wherein the radiation source includes an ultraviolet (UV) diode.

20. The catheter device of claim 18, wherein the radiation source is configured to reduce pathogenicity of pathogenic substances or microorganisms within the coupling cavity.

* * * * *